United States Patent
Pyun et al.

(10) Patent No.: US 11,672,425 B2
(45) Date of Patent: Jun. 13, 2023

(54) STAND-ALONE APPARATUS AND METHODS FOR IN VIVO DETECTION OF TISSUE MALIGNANCY USING LASER SPECTROSCOPY

(71) Applicant: Speclipse, Inc., Seoul (KR)

(72) Inventors: Sung Hyun Pyun, Seoul (KR); Wanki Min, Gyeonggi-do (KR)

(73) Assignee: SPECLIPSE, INC., Gyeonggi-do (KR)

( * ) Notice: Subject to any disclaimer, the term of this patent is extended or adjusted under 35 U.S.C. 154(b) by 446 days.

(21) Appl. No.: 16/101,928

(22) Filed: Aug. 13, 2018

(65) Prior Publication Data
US 2019/0246908 A1 Aug. 15, 2019

Related U.S. Application Data

(60) Provisional application No. 62/647,031, filed on Mar. 23, 2018.

(30) Foreign Application Priority Data

Feb. 15, 2018 (KR) .......................... 10-2018-0018857
Jun. 26, 2018 (KR) .......................... 10-2018-0073304

(51) Int. Cl.
G16H 50/20 (2018.01)
A61B 5/00 (2006.01)
(Continued)

(52) U.S. Cl.
CPC .......... *A61B 5/0084* (2013.01); *A61B 5/0013* (2013.01); *A61B 5/0071* (2013.01);
(Continued)

(58) Field of Classification Search
CPC ..... A61B 5/0084; A61B 5/0071; A61B 5/441; A61B 5/0013; A61B 5/726; A61B 5/4836;
(Continued)

(56) References Cited

U.S. PATENT DOCUMENTS 5,608,520 A 3/1997 Fleming
6,135,965 A * 10/2000 Turner ................. A61B 5/0071
128/925
(Continued)

FOREIGN PATENT DOCUMENTS

JP 2001-505113 A 4/2001
JP 2003-512085 A 4/2003
(Continued)

OTHER PUBLICATIONS

Alvira et al., "Qualitative evaluation of Pb and Cu in fish using laser-induced breakdown spectroscopy with multipulse excitation by ultracompact laser source", May 10, 2015, Applied Optics, vol. 54, No. 14, pp. 4453-4457 (Year: 2015).*

(Continued)

*Primary Examiner* — Patricia J Park
*Assistant Examiner* — Adil Partap S Virk
(74) *Attorney, Agent, or Firm* — Harness, Dickey & Pierce, P.L.C.

(57) ABSTRACT

According to an embodiment of the present disclosure, there is provided a laser spectroscopy-based independent device, including: a spectrometer configured to measure a spectrum of generated light which is generated by a laser projected onto a sample; and a disease analysis module configured to determine whether there is lesion tissue by applying a lesion tissue detection learning model to a result of non-discrete spectrum measurement, which is measured by the spectrometer, wherein the spectrometer is configured to measure spectra of all generated light that is generated from a time when the laser is projected onto the sample.

8 Claims, 7 Drawing Sheets

(51) Int. Cl.
  *G01J 3/443* (2006.01)
  *G01N 21/71* (2006.01)
  *G01J 3/02* (2006.01)

(52) U.S. Cl.
  CPC ............ *A61B 5/0075* (2013.01); *A61B 5/414* (2013.01); *A61B 5/441* (2013.01); *A61B 5/444* (2013.01); *A61B 5/4836* (2013.01); *A61B 5/726* (2013.01); *G01J 3/0218* (2013.01); *G01J 3/443* (2013.01); *G01N 21/718* (2013.01); *G16H 50/20* (2018.01); *A61B 2560/0233* (2013.01)

(58) Field of Classification Search
  CPC ....... A61B 5/0075; A61B 5/414; A61B 5/444; A61B 2560/0233; A61B 5/7267; G01J 3/443; G01J 3/0218; G01J 3/28; G16H 50/20; G01N 21/718
  See application file for complete search history.

(56) References Cited

U.S. PATENT DOCUMENTS

| | | | |
|---|---|---|---|
| 7,092,087 | B2 | 8/2006 | Kumar et al. |
| 10,650,929 | B1 * | 5/2020 | Beck ............... G16H 50/70 |
| 11,085,882 | B1 * | 8/2021 | Bol'shakov ........ G01N 21/718 |
| 2005/0090751 | A1 | 4/2005 | Balas |
| 2008/0118912 | A1 * | 5/2008 | Dickson ................ B82Y 15/00 435/6.12 |
| 2008/0221457 | A1 | 9/2008 | Zeng et al. |
| 2009/0312644 | A1 | 12/2009 | Kosugi et al. |
| 2011/0171636 | A1 * | 7/2011 | Melikechi ............ G01N 21/718 435/7.1 |
| 2014/0270457 | A1 * | 9/2014 | Bhargava ............. G06T 7/0014 382/133 |
| 2015/0025343 | A1 | 1/2015 | Gareau et al. |
| 2015/0335248 | A1 | 11/2015 | Huang et al. |
| 2015/0377787 | A1 * | 12/2015 | Zeng .................... A61B 5/0075 356/301 |
| 2016/0166194 | A1 | 6/2016 | Gareau et al. |
| 2016/0235372 | A1 * | 8/2016 | Schneider ............... G16Z 99/00 |
| 2017/0023484 | A1 * | 1/2017 | Wang .................... G01J 3/0237 |
| 2017/0175169 | A1 | 6/2017 | Lee et al. |
| 2018/0020956 | A1 | 1/2018 | Lee et al. |
| 2018/0098726 | A1 | 4/2018 | Pyun et al. |
| 2018/0360390 | A1 * | 12/2018 | Gaudiuso ............. A61B 5/4325 |
| 2019/0133514 | A1 | 5/2019 | Gareau et al. |
| 2019/0246908 | A1 | 8/2019 | Pyun et al. |
| 2019/0246971 | A1 * | 8/2019 | Pyun ..................... A61B 5/0075 |
| 2019/0261913 | A1 * | 8/2019 | Beaulieu ............. A61B 5/0084 |
| 2019/0274619 | A1 | 9/2019 | Gareau et al. |

FOREIGN PATENT DOCUMENTS

| | | |
|---|---|---|
| JP | 2009-300131 A | 12/2009 |
| JP | 2010-249835 A | 11/2010 |
| JP | 2016-510245 A | 4/2016 |
| JP | 5915543 B2 | 5/2016 |
| JP | 2016-530917 A | 10/2016 |
| KR | 10-1997-0061214 | 9/1997 |
| KR | 10-2015-0036345 A | 4/2015 |
| KR | 10-2017-0058958 A | 5/2017 |
| KR | 10-2017-0106776 A | 9/2017 |
| KR | 10-2017-0114897 A | 10/2017 |
| KR | 10-2017-0114973 A | 10/2017 |
| KR | 10-2018-0011646 A | 2/2018 |
| WO | WO-2018/075679 A1 | 4/2018 |

OTHER PUBLICATIONS

Office Action from corresponding Korean Patent Application No. 10-2018-0073304, dated Jan. 17, 2020.
Office Action from corresponding Korean Patent Application No. 10-2018-0073310, dated Jan. 17, 2020.
International Search Report from corresponding PCT Application No. PCT/KR2018/007301, dated Oct. 17, 2018.
International Search Report from corresponding PCT Application No. PCT/KR2018/007297, dated Oct. 26, 2018.
Office Action from corresponding U.S. Appl. No. 16/043,689, dated Sep. 18, 2020.
Notice of Allowance from corresponding Korean Patent Application No. 10-2018-0073304, dated Sep. 19, 2020.
Office Action from corresponding Korean Patent Application No. 10-2018-0073310, dated Sep. 18, 2020.
Written Opinion of PCT Application No. PCT/KR2018/007301, dated Oct. 17, 2018.
Written Opinion of PCT Application No. PCT/KR2018/007297, dated Oct. 26, 2018.
International Search Report of PCT Application No. PCT/KR2019/010811, dated Dec. 28, 2019.
Written Opinion of PCT Application No. PCT/KR2019/010811, dated Dec. 28, 2019.
2nd Office Action of Korean Patent Application No. 10-2019-0104041, dated Dec. 26, 2019.
Final Rejection of Korean Patent Application No. 10-2019-0104041, dated Apr. 17, 2020.
Notice of Allowance of Korean Patent Application No. 10-2019-0104041, dated Jun. 12, 2020.
Office Action of Korean Patent Application No. 10-2019-0104039, dated Nov. 20, 2020.
Office Action of Korean Patent Application No. 10-2019-0104040, dated Nov. 20, 2020.
Office Action of Korean Patent Application No. 10-2019-0104042, dated Nov. 20, 2020.
Office Action of Korean Patent Application No. 10-2019-0104043, dated Nov. 20, 2020.
1st Notice of Allowance of U.S. Appl. No. 16/863,140, dated Jul. 14, 2020.
2nd Notice of Allowance of U.S. Appl. No. 16/863,140, dated Nov. 4, 2020.
3rd Notice of Allowance of U.S. Appl. No. 16/863,140, dated Mar. 31, 2021.
Office Action from corresponding Korean Patent Application No. 10-2019-0104043, dated Jun. 8, 2021.

* cited by examiner

STAND-ALONE APPARATUS AND METHODS FOR IN VIVO DETECTION OF TISSUE MALIGNANCY USING LASER SPECTROSCOPY

CROSS-REFERENCE TO RELATED APPLICATIONS

This application claims the benefit under 35 U.S.C. § 119 from Korean Patent Application No. 10-2018-0018857, filed on Feb. 15, 2018, in the Korean Intellectual Property Office, U.S. Provisional Application No. 62/647,031, filed on Mar. 23, 2018, in the United States Patent and Trademark Office, and Korean Patent Application No. 10-2018-0073304, filed on Jun. 26, 2018, in the Korean Intellectual Property Office, the disclosure of which is incorporated herein by reference in its entirety.

FIELD

The present disclosure relates to a laser spectroscopy-based independent device for in-vivo detection of lesion tissue and a method therefor.

BACKGROUND

Technology for diagnosing diseases by irradiating animal or human body tissues with lasers and analyzing spectra of generated light is disclosed in the related art. For example, U.S. Pat. No. 7,092,087 (Aug. 15, 2006) (hereinafter, US'087 patent) discloses a technical concept of diagnosing diseases of animals.

However, the technology disclosed in US'087 patent described above detects lesion tissue with reference to a threshold value regarding specific components in a wavelength region, and does not guarantee accuracy.

SUMMARY

According to an embodiment of the present disclosure, there is provided a laser spectroscopy-based independent device for in-vivo or ex-vivo detection of lesion tissue.

According to another embodiment of the present disclosure, there are provided devices used in a laser spectroscopy-based device for in-vivo or ex-vivo detection of lesion tissue.

According to another embodiment of the present disclosure, there is provided a machine learning-based lesion tissue detection method.

According to an embodiment of the present invention, there is provided a laser spectroscopy-based independent device, including: a spectrometer configured to measure a spectrum of generated light which is generated by a laser projected onto a sample; and a disease analysis module configured to determine whether there is lesion tissue by applying a lesion tissue detection learning model to a result of non-discrete spectrum measurement, which is measured by the spectrometer, wherein the spectrometer is configured to measure spectra of all generated light that is generated from a time when the laser is projected onto the sample.

According to another embodiment of the present invention, there is provided a machine learning-based lesion tissue detection method, including: a non-discrete spectrum measurement step of measuring spectra of all generated light which is generated from a time when a laser is projected onto a sample until the generated light is no longer generated; and a step of determining whether there is lesion tissue by applying a lesion tissue detection learning model to a result of the non-discrete spectrum measurement.

According to one or more embodiments of the present disclosure, a lesion can be more exactly detected through non-discrete spectrum measurement and a machine learning-based lesion tissue detection method.

In addition, the present embodiments may support both in-vivo lesion detection and ex-vivo lesion detection.

EXPLANATION OF SIGNS

Figure 1:
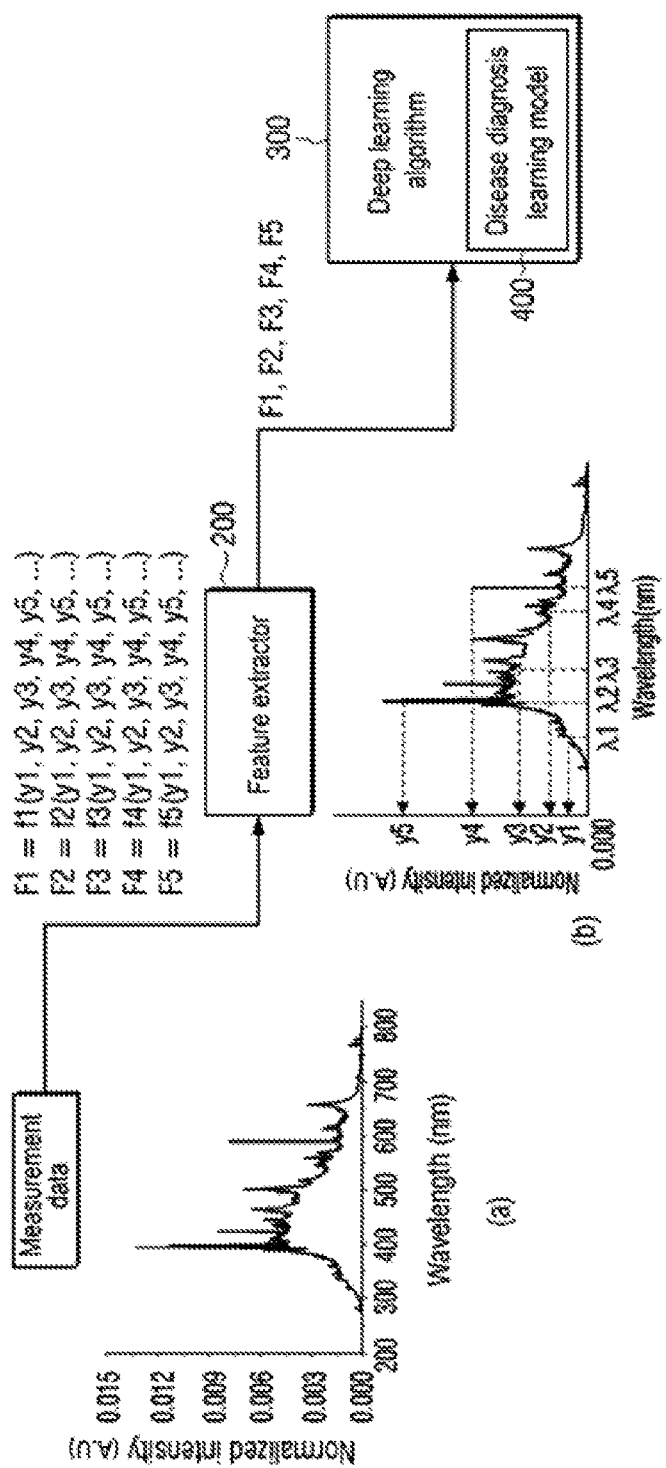
FIGS. 1, 2, and 3 are views to illustrate a machine learning-based lesion tissue detection method according to an embodiment of the present disclosure.

| | |
|---|---|
| 10: analysis unit | 11: laser |
| 13, 15: optical elements | 20: handpiece |
| 21: spectrometer | 23: disease analysis module |
| 25: power source | 27: display |
| 30: cable | |

DETAILED DESCRIPTION

Exemplary embodiments will now be described more fully with reference to the accompanying drawings to clarify aspects, other aspects, features and advantages of the present invention. The exemplary embodiments may, however, be embodied in many different forms and should not be construed as limited to the exemplary embodiments set forth herein. Rather, the exemplary embodiments are provided so that this invention will be thorough and complete, and will fully convey the scope of the application to those of ordinary skill in the art.

The terms "unit," "device," and "module" used in the following description refer to a unit for processing at least one function or operation, and may be implemented by hardware, software, or a combination of hardware and software.

The terms used in the following description are for the purpose of describing particular exemplary embodiments only and are not intended to limit the present invention. As used herein, the singular forms are intended to include the plural forms as well, unless the context clearly indicates otherwise. It will be further understood that the terms "comprises" and/or "comprising," when used in this specification, do not preclude the presence or addition of one or more other components.

Definition of Terms

In the detailed description of this application, the term "program" or "algorithm" refers a "set of commands appropriate to processing by a computer," and the "programs" and the "algorithm" are used as having the same meaning.

In the detailed description of this application, the expression "a program (or algorithm) performs (or executes) a certain operation (or step)" means that "the program (or algorithm) causes an electronic device provided with a processor to perform or execute the certain operation (or step)."

In the detailed description of this application, the term "laser" means a pulse laser or a continuous light laser. In addition, the frequency band of the "laser" may have a certain frequency band, and may have, for example, an ultra violet (UV) band, a visible light band, or an infrared (IR) band.

In the detailed description of this application, the term "generated light" encompasses all types of light which are generated when a laser is projected onto a sample T. Accordingly, the "generated light" may refer to plasma light, reflected light, scattered light, and/or fluorescence emission.

In the detailed description of this application, the term "sample" refers to biological tissue, and for example, may be human body tissue or animal tissue. In the detailed description of this application, the term "measurement data" refers to "spectrum data measured by a spectrometer regarding non-gated generated light that is generated when a laser is projected onto a sample," and may be data measured by non-discrete spectrum measurement.

In the detailed description of this application, all generated light that is measured from a time when a laser is projected onto a sample surface until the generated light is no longer generated is referred to as "non-gated generated light," and data that is measured by a spectrometer regarding the non-gated generated light is referred to as non-discrete spectrum measurement data or non-discrete spectrum data. The non-discrete spectrum measurement data or the non-discrete spectrum data is a concept including filtered non-discrete spectrum data.

In the detailed description of this application, the term "non-discrete spectrum measurement" refers to measuring spectra of all generated light that is generated from a time when a laser is projected onto a sample until the generated light is no longer generated, that is, non-gated generated light. That is, a result of the "non-discrete spectrum measurement" has values that are not discrete, that is, are continuous, in a wavelength band. The "non-discrete spectrum measurement" is a concept including "filtered non-discrete spectrum measurement."

In the detailed description of this application, the term "filtered non-discrete spectrum measurement" refers to measuring a spectrum for some light of the non-gated generated light, or measuring a spectrum for light of the non-gated generated light that belongs to a specific wavelength band.

In the detailed description of this application, the term "filtered non-discrete spectrum" refers to data that is obtained as a result of performing "filtered non-discrete spectrum measurement."

In the detailed description of this application, the term "parameter of a feature extraction device" is used to indicate parameters (for example, a weight value and a principle component of a feature function) constituting the feature extraction device.

A machine learning-based lesion tissue detection method according to an embodiment of the present disclosure includes a preprocessing step (hereinafter, referred to as a "first step") and a determination step (hereinafter, referred to as a "second step").

The first step includes a step of normalizing a result of non-discrete spectrum measurement (NSM) regarding non-gated generated light, a step of standardizing, and a principle component analysis (PCA) step of extracting a feature of a principle component from the result of measurement which is normalized and standardized.

Herein, the steps of normalizing and standardizing are steps of removing a deviation and a noise between the results of measurement. For example, the steps of normalizing and standardizing may include area-normalization and interpolation operations after removing a background noise from the result of measurement.

The machine learning-based lesion tissue detection method according to an embodiment of the present disclosure may further include a step of performing non-discrete spectrum measurement (NSM) with respect to non-gated generated light. Herein, the step of performing the NSM is a step of measuring spectra for all generated light measured from a time when a laser is projected onto a sample until the generated light is no longer generated, that is, for non-gated generated light. According to an embodiment, the step of performing the NSM may be a step of performing 'filtered' non-discrete spectrum measurement to measure a spectrum for some light of the non-gated generated light or to measure a spectrum for light of the non-gated generated light that belongs to a specific wavelength band.

In embodiments of the present disclosure, the "result of the non-discrete spectrum measurement" refers to data undergoing "non-discrete spectrum measurement" as it is, or refers to data after normalizing and standardizing the data.

The machine learning-based lesion tissue detection method according to an embodiment of the present disclosure may further include a step of projecting a laser of a specific band onto a sample surface, and a step of performing NSM with respect to non-gated generated light. For example, a wavelength of the laser projected onto the sample surface may be 1064 nm. In addition, the step of performing the NSM may be a step of performing filtered non-discrete spectrum measurement to measure a spectrum for some light of the non-gated generated light or to measure a spectrum for light of the non-gated generated light that belongs to a specific wavelength band.

The principle component analysis (PCA) step is a step of extracting the feature regarding the principle component from the result of the non-discrete spectrum measurement. According to an embodiment, a plurality of principle components may be provided (referred to as a "multi dimension"), and the principle component analysis step includes an operation of extracting features (or "feature values") regarding the plurality of principle components.

According to an embodiment, the principle component analysis step may extract feature regarding 16-dimensional principle components. Herein, since the 16 dimensions are an exemplary numerical value, the present disclosure is not limited to this numerical value. The principle component analysis step may extract features regarding principle components in dimensions higher than 16 dimensions.

In embodiments of the present disclosure, "extracting features of a plurality of principle components" will be referred to as "multi-dimensional principle component analysis" for the sake of description.

The first step described above may be performed by an electronic device, including a memory (not shown), one or more processors (not shown), and one or more programs (not shown). Herein, the one or more programs (hereinafter, "programs for preprocessing") may be stored in the memory and may be configured to be executed by the one or more processors. Herein, the programs for preprocessing may include instructions for performing the steps of normalizing and standardizing, and the principle component analysis (PCA) step.

According to an embodiment, the programs for preprocessing may include a normalization and standardization program, and a multi-dimensional principle component analysis program. These programs include instructions for performing their respective operations.

According to an embodiment, the memory (not shown), the one or more processors (not shown), and the programs for preprocessing (not shown) for the first step may be disposed in an analysis device 10, which will be described below with reference to FIG. 4.

According to another embodiment, a portion of the memory (not shown), the one or more processors (not shown), and the programs for preprocessing (not shown) for the first step may be disposed in the analysis device 10, which will be described below with reference to FIG. 4, and the other portion may be disposed in a handpiece 20.

According to still another embodiment, a portion of the memory (not shown), the one or more processors (not shown), and the programs for preprocessing (not shown) for the first step may be disposed in the analysis device 10, which will be described below with reference to FIG. 4, and the other portion may be disposed in an electronic device connected with the analysis device 10 via a communication network (or a network for transmitting or receiving data, for example, the Internet).

The second step is a step of determining whether there is lesion tissue in a sample by applying, by a machine learning algorithm, a classifier, which is a learning model for detecting lesion tissue, to the result of the multi-dimensional principle component analysis in the first step.

The lesion tissue detection learning model may be a classifier that is generated by being trained by (or learning from) labelled non-discrete spectrum measurement data. According to an embodiment, the non-discrete spectrum measurement data may be filtered non-discrete spectrum data.

According to an embodiment, the machine learning algorithm is a deep learning algorithm that is configured to include an input layer, at least one hidden layer, and an output layer. Herein, the hidden layer may be a layer that reflects functions and coefficients constituting the lesion tissue detection learning model.

The input layer receives the result of the preprocessing step, the hidden layer applies the lesion tissue detection learning model to the data received by the input layer, and the output layer outputs a result on the hidden layer. The output value of the output layer may be a value indicating the presence/absence of lesion tissue as a probability.

The machine learning algorithm used in embodiments of the present disclosure may be, for example, logistic regression, space vector machine (SVM), random forest, deep neural network (DNN), or convolutional neural network (CNN). It will be understood by persons having an ordinary skill in the art ("those skilled in the art") to which the present disclosure pertains that the present disclosure is not limited to the above-described algorithms.

The second step described above may be performed by an electronic device, including a memory (not shown), one or more processors (not shown), and one or more programs (not shown). Herein, the one or more programs (hereinafter, "machine learning programs") may be stored in the memory and may be configured to be executed by the one or more processors.

According to an embodiment, the machine learning program may include instructions for performing the above-described step of determining the presence/absence of lesion tissue. The machine learning program may further include instructions for performing a learning step for generating the lesion tissue detection learning model.

According to an embodiment, the memory (not shown), the one or more processors (not shown), and the machine learning program (not shown) for the second step may be disposed in the analysis device 10, which will be described below with reference to FIG. 4.

According to another embodiment, a portion of the memory (not shown), the one or more processors (not shown), and the machine learning programs (not shown) for the second step may be disposed in the analysis device 10, which will be described below with reference to FIG. 4, and the other portion may be disposed in the handpiece 20.

According to still another embodiment, a portion of the memory (not shown), the one or more processors (not shown), and the machine learning program (not shown) for the second step may be disposed in the analysis device 10, which will be described below with reference to FIG. 4, and the other portion may be disposed in an electronic device connected with the analysis device via a communication network (or a network for transmitting or receiving data, for example, the Internet).

The machine learning-based lesion tissue detection method according to an embodiment of the present disclosure may further include a step of determining a parameter of a feature extractor from the labelled non-discrete spectrum measurement data, and a step of defining the classifier which is the lesion tissue detection learning model by learning. Herein, the non-discrete spectrum measurement data may be, for example, filtered non-discrete spectrum data.

The step of determining the parameter of the feature extractor described above is a step of receiving, by the feature extractor, the labelled non-discrete spectrum measurement data, and determining the parameter of the feature extractor.

The step of defining the classifier by learning described above is a step of training the machine learning program based on the labelled non-discrete spectrum measurement data.

Herein, the classifier that is generated by being trained based on the labelled non-discrete spectrum measurement data may perform the step of determining whether there is lesion tissue based on unknown non-discrete spectrum measurement data.

Figure 2:
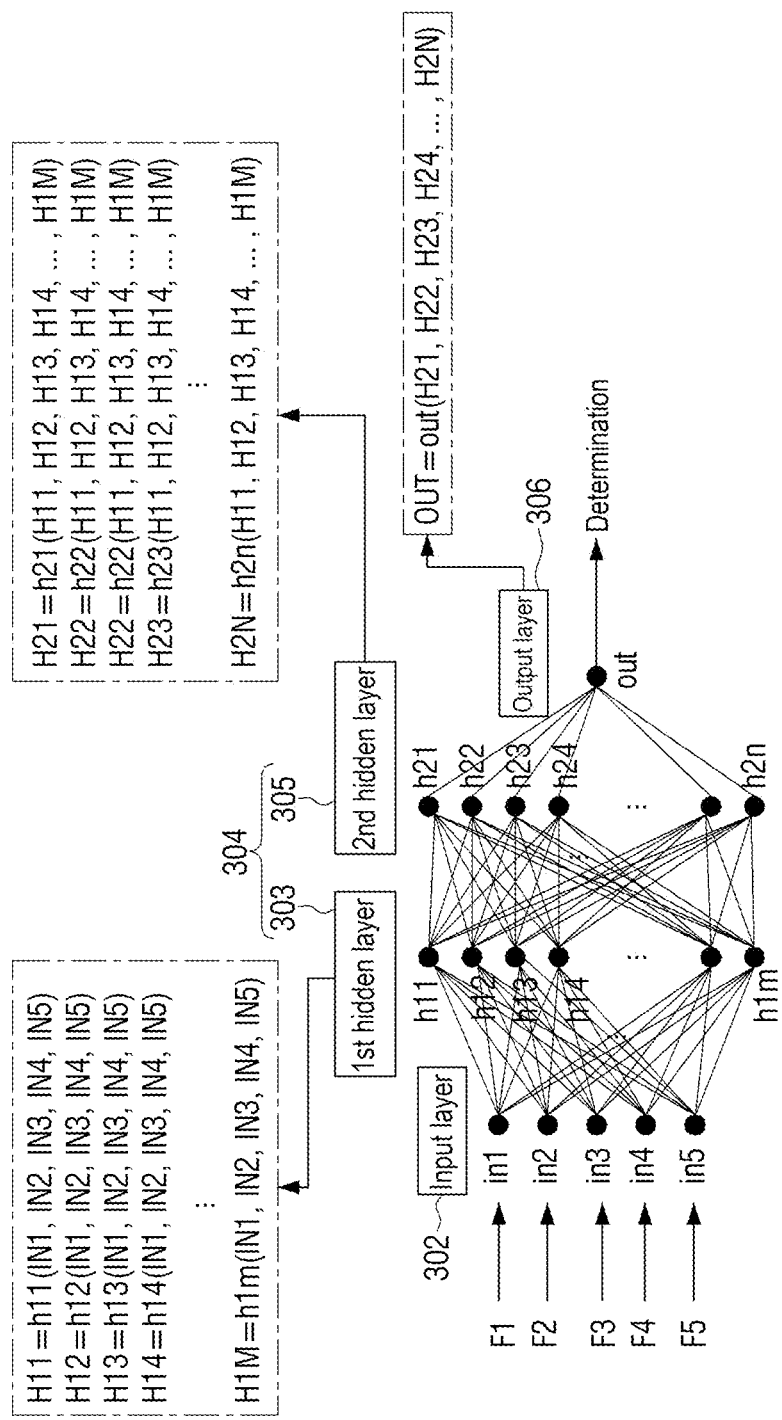
Figure 3:
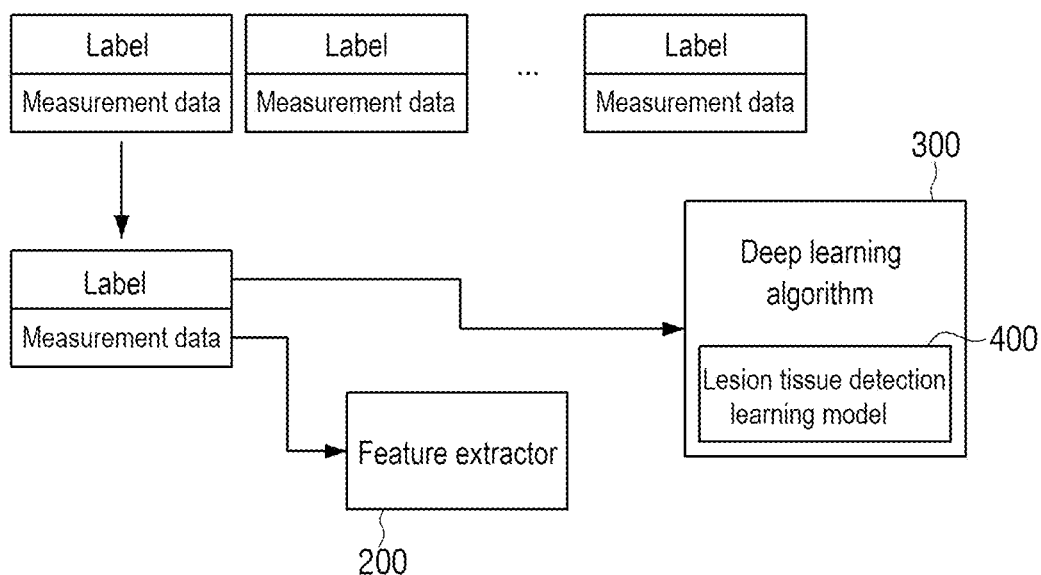

FIGS. 1 to 3 are views to illustrate a machine learning-based lesion tissue detection method according to an embodiment of the present disclosure.

Those skilled in the art should know that the machine learning-based lesion tissue detection method to be described with reference to these drawings uses a deep learning algorithm, and numerical values or functions mentioned below are examples and the scope of the present disclosure are not limited to those numerical values or functions.

Referring to FIG. 1, a feature extractor 200 is a program ("multi-dimensional principle component analysis program") that extracts features regarding principle components from non-discrete spectrum measurement data, and a lesion tissue detection learning model 400 is a classifier for determining the presence/absence of a lesion. Herein, the non-discrete spectrum measurement data may be, for example, filtered non-discrete spectrum data.

According to an embodiment, the feature extractor 200 extracts features regarding a plurality of principle components.

In the present embodiment, features regarding five principle components are extracted as shown in FIG. 1, for the sake of description.

That is, it is assumed that the feature extractor 200 receives non-discrete spectrum measurement data as shown in view (a) of FIG. 1, and extracts features regarding five principle components from the measurement data.

In the present embodiment, the feature extractor 200 calculates values of functions f1, f2, f3, f4, f5 which receive, as inputs, intensities y1, y2, y3, y4, y5, . . . of respective signals of components λ1, λ2, λ3, λ4, λ5, . . . in a wavelength band.

In the present embodiment, the functions f1, f2, f3, f4, f5 calculated by the feature extractor 200 may have different coefficients (weight values) with respect to inputs.

For example, when it is assumed that an equation of f1 (y1, y2, y3, y4, y5, . . . )=(a1*y1)+(b1*y2)+(c1*y3)+(d1*y4)+(e1*y5)+ . . . is defined, and an equation of f2(y1, y2, y3, y4, y5, . . . )=(a2*y1)+(b2*y2)+(c2*y3)+(d2*y4)+(e2*y5)+ . . . is defined, a1 and a2 may be different from each other, b1 and b2 may be different from each other, c1 and c2 may be different from each other, d1 and d2 may be different from each other, and/or e1 and e2 may be different from each other.

Referring to FIG. 1, the feature extractor 200 outputs the features that are calculated by the feature extraction functions.

In the present embodiment, when it is assumed that the feature extractor 200 has five (that is, five-dimensional) feature extraction functions, the five feature extraction functions F1, F2, F3, F4, F5 may calculate and output respective function values, and the outputs may be inputted to a deep learning algorithm 300.

The deep learning algorithm 300 may determine the presence/absence of lesion tissue by applying the lesion tissue detection learning model 400 to the inputted features.

FIG. 2 is a view to illustrate the deep learning algorithm 300.

According to an embodiment, the deep learning algorithm 300 may receive the features from the feature extractor 200, and may determine the presence/absence of lesion tissue by applying the lesion tissue detection learning model 400 to the features.

In the present embodiment, the deep learning algorithm 300 configured to include an input layer 302, hidden layers 304 (a first hidden layer 303, a second hidden layer 305), and an output layer 306 will be described by way of an example for the sake of description.

Each of the input layer 302, the hidden layers 304, and the output layer 306 may be formed of one or more nodes, and each of the nodes may receive a plurality of inputs, and may have the same number of coefficients (or "weight values") as the number of inputs. That is, the node performs an operation of calculating predetermined coefficients with respect to the inputs received thereby. In addition, the weight values calculated for the inputs at the node may be defined differently according to nodes.

Referring to FIG. 2, the input layer 302 may be formed of five nodes, and the five nodes (hereinafter, "input nodes") may receive the five features extracted by the feature extractor 200, and may output the features to the hidden layers 304.

Referring to FIG. 2, for the sake of description, the five inputs nodes are expressed by in1, in2, in3, in4, and in5, and respective outputs of in1, in2, in3, in4, and in5 are expressed by IN1, IN2, IN3, IN4, and IN5. Herein, IN1 may be the inputted feature F1 as it is, or may be a value of a certain function receiving F1 as an input.

The first hidden layer 303 may be formed of a plurality of nodes (hereinafter, "first hidden nodes"), and the first hidden nodes may calculate functions receiving the output values of the input nodes as inputs, and may output the functions. Referring to FIG. 2, the number of the plurality of first hidden nodes is m (herein, m is a positive integer), and the first hidden nodes are expressed by h11, h12, h13, h14, . . . , h1m.

FIG. 2 illustrates the respective functions calculated at the m first hidden nodes, and their operations by way of an example.

For the sake of description, a function applied at the node h11 of the first hidden nodes is defined as h11, and a result (or "output") of the function h11 is defined as H11. In addition, the function h11 receiving IN1, IN2, IN3, IN4, and IN5 as inputs may be defined by an equation of H11=h11 (IN1, IN2, IN3, IN4, IN5). That is, the node h11 of the first hidden nodes may calculate the function h11 receiving IN1, IN2, IN3, IN4, and IN5 as inputs, and may output the result H11 of the calculation.

The other nodes h11, h13, h14, . . . , h1m of the first hidden nodes may be expressed and defined by equations in a similar method. That is, the node h12 of the first hidden nodes may calculate the function h12 receiving IN1, IN2, IN3, IN4, and IN5 as inputs, and may output the result H12 of the calculation.

In the same way, the other first hidden nodes may output H13, H14, . . . , H1M.

According to an embodiment, the coefficients included in the functions h11, h12, h13, h14, . . . , h1m calculated at the first hidden nodes may be different in at least one function h11, h12, h13, h14, . . . , h1m.

For example, when it is assumed that an equation of H11=h11(IN1, IN2, IN3, IN4, IN5)=(f11*IN1)+(g11*IN2)+(j11*IN3)+(k11*IN4)+(p11*IN5) is defined, and an equation of H12=h12(IN1, IN2, IN3, IN4, IN5)=(f12*IN1)+(g12*IN2)+(j12*IN3)+(k12*IN4)+(p12*IN5) is defined, f11 and f12 may be different from each other, g11 and g12 may be different from each other, j11 and j12 may be different from each other, k11 and k12 may be different from each other, and/or p11 and p12 may be different from each other.

That is, the function of the node h11 of the first hidden layer 303 may be defined to receive IN1, IN2, IN3, IN4, and IN5 as inputs, and to calculate weight values corresponding to these inputs, and the function of the node h12 of the first hidden nodes may be defined to receive IN1, IN2, IN3, IN4, and IN5 as inputs, and to calculate weight values of these inputs. At least one of the weight values used in the function of the node h11, and at least one of the weight values used in the function of the node h12 may be different from each other. In the same way, at least one of the weight values used in the functions included in the first hidden nodes may be different from at least one weight value.

The second hidden layer 305 may be formed of a plurality of nodes (hereinafter, "second hidden nodes"), and the second hidden nodes calculate and output functions receiving the output values of the first hidden nodes as variables. Referring to FIG. 2, the number of the plurality of second hidden nodes may be n (herein, n is a positive integer), and the second hidden nodes are expressed by h21, h22, h23, h24, . . . , h2n.

FIG. 2 illustrates the respective functions calculated at the n second hidden nodes, and their operations by way of an example.

For the sake of description, a function applied at the node h21 of the second hidden nodes is defined as h21, and a result of the function h21 is defined as H21. In addition, the function h21 receiving H11, H12, H13, H14, . . . , H1M as input parameters may be defined by an equation of H21=h21 (H11, H12, H13, H14, . . . , H1M). That is, the node h21 of the second hidden nodes may calculate the function h21 receiving H11, H12, H13, H14, . . . , H1M as input parameters, and may output the result H21 of the calculation.

The other nodes h22, h23, h24, . . . , h2n of the second hidden nodes may be expressed and defined by equations in a similar method. That is, the node h22 of the second hidden nodes may calculate the function h22 receiving H11, H12, H13, H14, . . . , H1M as input parameters, and may output the result H22 of the calculation.

In the same way, the other second hidden nodes may output H23, H24, . . . , H2N.

According to an embodiment, the coefficients included in the functions h21, h22, h23, h24, . . . , h2n calculated at the second hidden nodes may be different in at least one function h21, h22, h23, h24, . . . , h2n.

For example, when it is assumed that an equation of H21=h21(H11, H12, H13, H14, . . . , H1M)=(f21*H11)+ (g21*H12)+(j21*H13)+(k21*H14)+ . . . +(p21*H1M) is defined, and an equation of H22=h22(H11, H12, H13, H14, . . . , H1N)=(f22*H11)+(g22*H12)+(j22*H13)+(k22*H14)± . . . +(p22*H1M) is defined, f21 and f22 may be different from each other, g21 and g22 may be different from each other, j21 and j22 may be different from each other, k21 and k22 may be different from each other, and/or p21 and p22 may be different from each other.

That is, the function of the node h21 of the second hidden nodes may be defined to receive H11, H12, H13, H14, . . . , H1M as parameters, and to calculate weight values corresponding to these parameters, and the function of the node h22 of the second hidden nodes may be defined to receive H11, H12, H13, H14, . . . , H1M as parameters, and to calculate weight values of these parameters. However, at least one of the weight values used in the function of the node h21, and at least one of the weight values used in the function of the node h22 may be different from each other.

In the same way, at least one of the weight values used in the functions included in the second hidden nodes may be different from at least one weight value.

The output layer 306 may be formed of one node (hereinafter, "output node"), and the output node may calculate and output a predetermined function receiving the output values of the second hidden nodes as an input. FIG. 2 illustrates the function calculated at the output node and an operation by way of an example.

For the sake of description, the function of the output node is defined as out, and a result of the function out is defined as OUT. In addition, the output function receiving H21, H22, H23, H24, . . . , H2N as input parameters may be defined by an equation of OUT=out(H21, H22, H23, H24, . . . , H2N). That is, the output node may calculate the function out receiving H21, H22, H23, H24, . . . , H2N as input parameters, and may output the result OUT of the calculation.

In the present embodiment, OUT may be a value that determines the presence/absence of lesion tissue. For example, OUT may be a value that is defined by 0≤OUT≤1 (OUT is a real number), or 0≤OUT≤100 (OUT is a percentage value).

The deep learning algorithm 300 may generate the lesion tissue detection learning model 400 by learning from the labelled measurement data.

Functions (hereinafter, "hidden node functions") correspond to the hidden nodes one by one, and the hidden nodes output the values of the hidden node functions corresponding thereto when receiving inputs.

The functions of the hidden nodes mathematically calculate the inputs and the coefficients (for example, multiplication). Learning by the lesion tissue detection learning model 400 will be described in detail below with reference to FIG. 3.

The lesion tissue detection learning model 400 is a model that is optimized by learning (or training). Training the lesion tissue detection learning model 400 refers to a process of optimizing the coefficients included in the functions of the nodes of the hidden layers. Learning will be described in detail below with reference to FIG. 3.

According to an alternative embodiment, the deep learning algorithm 300 may directly receive the measurement data, not through the feature extractor 200, and may determine the presence/absence of lesion tissue by applying the lesion tissue detection learning model 200. That is, the deep learning algorithm 300 may determine the presence/absence of lesion tissue by applying the lesion tissue detection learning model 400 to all values of a wavelength band, without using the feature extractor 200.

A learning operation according to an embodiment of the present disclosure will be described with reference to FIG. 3.

Referring to FIG. 3, the feature extractor 200 may optimally determine parameters of the feature extractor 200 by using a plurality of labelled measurement data, and the deep learning algorithm 300 trains the lesion tissue detection learning model 400 by using the plurality of labelled measurement data. Herein, the plurality of labelled measurement data may be, for example, filtered non-discrete spectrum data. In the detailed description of this application, the lesion tissue detection learning model after being trained will be referred to as a classifier.

A label indicates the presence/absence of lesion tissue. For example, measurement data labelled "cancer" refers to non-discrete spectrum measurement data that is collected from tissues of patients diagnosed with cancer by doctors.

A method for determining parameters of the feature extractor will be described first by way of an example.

The feature extractor 200 receives all measurement data (all measurement data collected) labelled (for example, labelled with cancer), and may determine parameters of the feature extractor 200 to effectively classify the measurement data.

According to an embodiment, the feature extractor 200 may determine weight values included in the functions of extracting features as optimized values.

According to another embodiment, the feature extractor 200 may determine not only the weight values included in the functions of extracting features, but also principle components (the number of principle components and/or locations of the principle components) as optimized values.

According to still another embodiment, the feature extractor 200 may determine the weight values included in the functions of extracting features as optimized values, and the principle components may be defined by a person (for example, a person implementing the present disclosure).

According to embodiments, the feature extractor 200 may determine the weight values included in the functions of extracting features as optimized values, based on the number of principle components and/or the locations of the principle components defined by the person implementing the present disclosure.

A method for optimizing the lesion tissue detection learning model 400 by training will be described by way of an example.

The deep learning algorithm 300 updates the coefficients constituting the lesion tissue detection learning model 400, while receiving measurement data (all measurement data collected) labelled (for example, labelled with cancer) in sequence.

The method described with reference to FIG. 3 is an example, and the present disclosure is not limited thereto. In the above-described embodiments, specific numerical numbers are examples, and thus it should be understood by those skilled in the art that the present disclosure is not limited to these numerical values.

Figure 4:
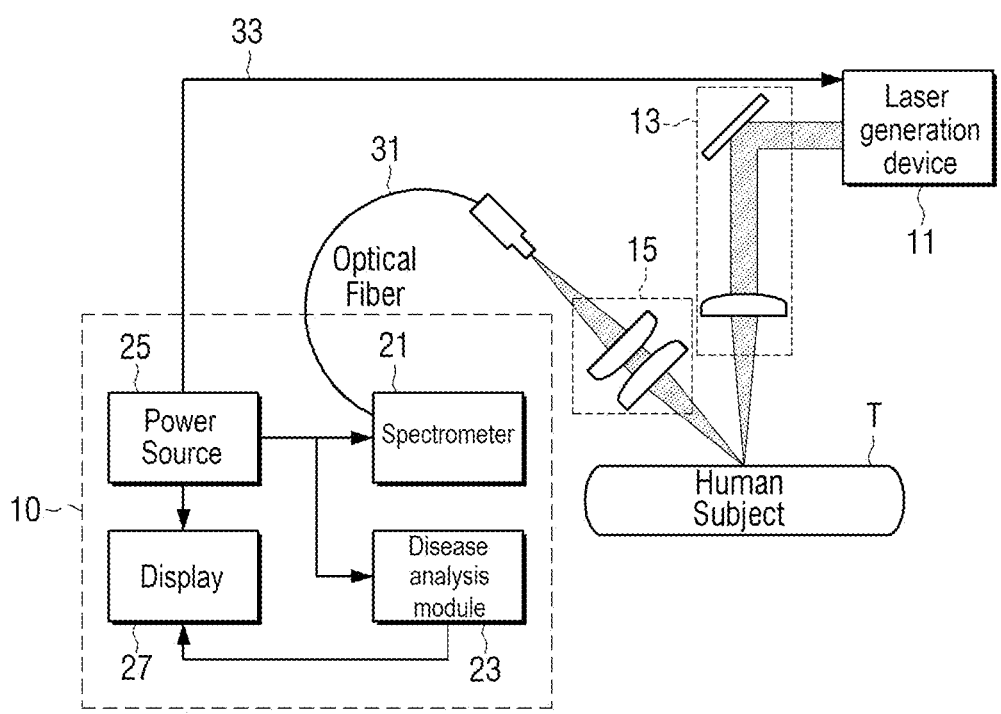
FIG. 4 is a view to illustrate an independent device based on laser spectroscopy, for detecting lesion tissue, according to an embodiment of the present disclosure.

FIG. 4 is a view to illustrate an independent device based on laser spectroscopy for detecting lesion tissue (hereinafter, an "independent device") according to an embodiment of the present disclosure.

Referring to FIG. 4, the independent device according to an embodiment of the present disclosure may determine whether there is lesion tissue in a sample, by irradiating the sample T with a laser, collecting generated light generated from the sample T, and analyzing spectra of the collected light according to the above-described "machine learning-based lesion tissue detection method."

The present independent device may make an ex-vivo lesion diagnosis as well as an in-vivo lesion diagnosis.

The independent device according to an embodiment of the present disclosure may diagnose a disease such as cancer. For example, the present independent device may diagnose a disease such as skin cancer, and also, may diagnose other types of cancer in addition to skin cancer.

The skin cancer may be, for example, squamous cell carcinoma, basal cell carcinoma, or melanoma.

Referring to FIG. 4, the independent device according to an embodiment of the present disclosure may include an analysis device 10, a laser generation device 11, first optical elements 13 for guiding a laser generated by the laser generation device 11 to be projected onto the sample T, second optical elements 15 for collecting generated light generated when the laser is projected onto the sample T, and a cable 31 providing a path through which the generated light collected by the second optical elements 15 travels to the analysis device.

According to an embodiment, the analysis device 10 is an electronic device that performs non-discrete spectrum measurement with respect to the non-gated generated light collected from the sample T and determines the presence/absence of lesion tissue by performing the first step and the second step with respect to the result of the measurement.

According to another embodiment, the analysis device 10 may additionally perform a step of determining parameters of the feature extractor extracting features, from labelled non-discrete spectrum measurement data, and a step of defining a lesion tissue detection learning model from the labelled non-discrete spectrum measurement data.

According to an embodiment, the analysis device 10 may include a plurality of electronic devices. For example, the analysis device 10 includes a spectrometer 21, a disease analysis module 23, a power source 25, and a display 27.

The spectrometer 21 performs non-discrete spectrum measurement with respect to the non-gated generated light collected from the sample T.

Figure 5:
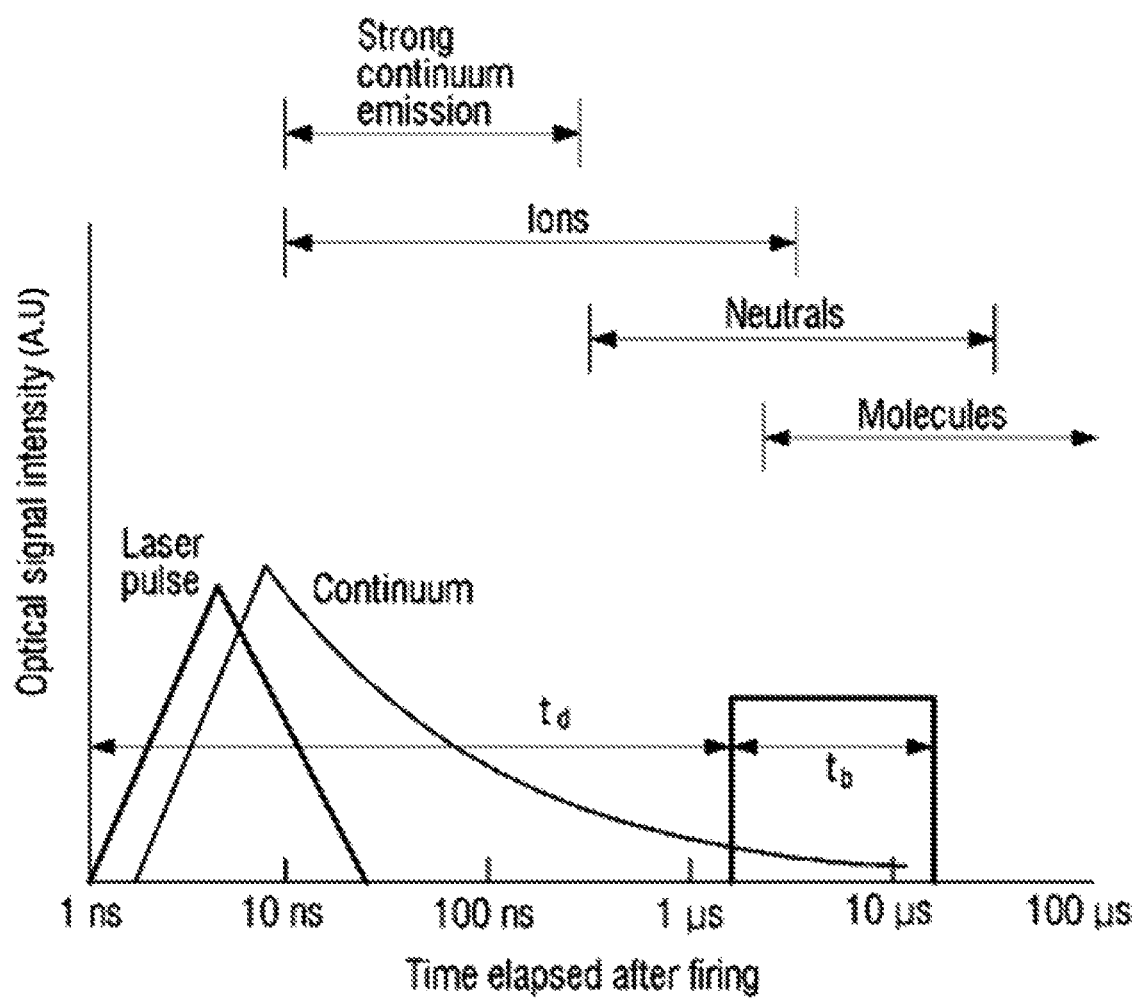
FIG. 5 is a view to illustrate non-discrete spectrum measurement according to an embodiment of the present disclosure.

FIG. 5 is a view to illustrate a non-discrete spectrum according to an embodiment of the present disclosure. In the present disclosure, it is important to use non-discrete spectrum measurement data, and hereinafter, the non-discrete spectrum will be described in detail with reference to FIG. 5.

In general, a pulse laser having a pulse length of a few nanoseconds or less (from fs to ns) is collected and projected onto the sample surface, and, when energy is greater than or equal to 1 $GW/cm^2$ on the sample surface, the sample surface is ablated by a minimum amount, and turns into a plasma.

In this case, "plasma light" (including an electronic emission from atoms and/or ions, molecular emission, and continuum emission, etc.) is generated on the sample surface. When gating of the spectrometer is performed after a predetermined time (for example, 1 μs) (that is, the generated light is measured after a predetermined time elapses after the laser is projected onto the sample surface) as shown in FIG. 5, the initial continuum emission spectrum may be excluded, and the spectrum of the electronic emission from atoms and/or ions may be normally obtained.

Compared with this, the spectrum of the non-gated generated light collected from the sample after the laser is projected onto the sample is non-discrete spectrum data including all of the spectrum of the electronic emission from atoms and/or ions, the molecular emission spectrum, and the continuum emission spectrum.

According to an embodiment of the present disclosure, the spectrometer 21 may measure the spectrum of the non-gated generated light.

According to another embodiment of the present disclosure, the spectrometer 21 is configured to measure a filtered non-discrete spectrum in the non-gated generated light.

For example, to measure the filtered non-discrete spectrum, the spectrometer 21 measure a spectrum for other light except for reflected light, scattered light, and fluorescence emission in the non-gated generated light, collected after the laser is projected onto the sample. That is, the spectrometer 21 is configured to perform a filtering operation to exclude reflected light, scattered light, and fluorescence emission from the non-gated generated light, and to measure a spectrum for the other light, and accordingly, obtains a non-discrete spectrum for the other light except for reflected light, scattered light, and fluorescence emission.

In another example, to measure the filtered non-discrete spectrum, the spectrometer 21 is configured to perform a filtering operation to measure a spectrum for plasma light in the non-gated generated light, collected after the laser is projected onto the sample. Due to this configuration, a non-discrete spectrum for the plasma light is obtained.

In still another example, to measure the filtered non-discrete spectrum, the spectrometer 21 is configured to measure a spectrum only for generated light of a specific wavelength band (200 nm to 1000 nm) in the non-gated generated light, collected after the laser is projected onto the sample. Due to this configuration, a non-discrete spectrum for the generated light of the specific wavelength band (200 nm to 1000 nm) is obtained.

The disease analysis module 23 is an electronic device that determines the presence/absence of lesion tissue in the sample T by performing the preprocessing step (first step) and the step (second step) of determining the presence/ absence of lesion tissue, in sequence, with respect to the result of the non-discrete spectrum measurement.

According to another embodiment, the disease analysis module 23 may additionally perform the step of determining parameters of the feature extractor from the labelled non-discrete spectrum measurement data, and the step of defining the lesion tissue detection learning model from the labelled non-discrete spectrum measurement data.

According to an embodiment, the disease analysis module 23 includes a memory (not shown), one or more processors (not shown), and one or more programs. Herein, the one or more programs may include programs for preprocessing and/or a deep learning program.

Herein, the programs for preprocessing may include a multi-dimensional principle component analysis program as a program for performing the preprocessing step, and the deep learning program performs the operation of determining the presence/absence of lesion tissue. Regarding these programs, please refer to the above descriptions.

The power source 25 supplies power to the laser generation device 11 and the disease analysis module 23.

The display 27 may output the result of the analysis by the disease analysis module 23 in such a form that a user can visually and/or acoustically recognize.

The laser generation device 11 may be generally used for the purpose of treating skin, for example.

When a pulse laser generated by the laser generation device 11 is collected and projected onto the sample surface, reflected light, scattered light, or fluorescence emission are generated in addition to plasma light.

According to an embodiment of the present disclosure, it is preferable to obtain a non-discrete spectrum only for the plasma light, except for the reflected light, scattered light, and fluorescence emission in the generated light generated when the pulse laser is collected and projected onto the sample surface.

For example, the laser generation device 10 projects a laser having a specific wavelength band to the sample surface, and the spectrometer 21 measures a spectrum only for generated light that belongs to the specific wavelength band in the generated light generated from the sample surface.

More specifically, a laser generation device, referred to as 'Q-switched Nd:YAG laser, may generate a laser of a wavelength of 1064 nm and 532 nm. When the laser of this wavelength is projected onto the sample surface, light having the wavelength band of 200 nm to 1000 nm may be generated as tissues of the sample break down. That is, the spectrum measured for the generated light having the wavelength band of 200 nm to 1000 nm includes the spectrum of the electronic emission from atoms and/or ions and the molecular emission spectrum. Accordingly, the spectrometer 21 may obtain a filtered non-discrete spectrum by measuring a spectrum only for the light having the wavelength band of 200 nm to 1000 nm (1 μm) in the generated light generated when the laser, referred to as Q-switched Nd: YAG laser, is projected on the sample surface.

When a source laser of a wavelength of 1064 nm is projected onto the sample surface, the wavelengths of reflected light, scattered light, and fluorescence emission are almost not changed at the wavelength of the source laser, and are maintained at 1064 nm. Although the wavelength of inelastic scattered light, which is a tiny portion of the scattered light, is changed, its signal strength is so weak in comparison to elastic scattered light, that the signal may be disregarded. The wavelengths (1064 nm) of the reflected light, scattered light, and fluorescence emission of the generated light may be completely separated from the wavelength band (200 nm to 1000 nm) in which the spectrum of the electronic emission from atoms and/or ions and the molecular emission spectrum to be measured are emitted.

According to the present embodiment, the laser generation device 11 is configured to generate the laser of the wavelength of 1064 nm and to project the laser onto the sample surface, and the spectrometer 21 is configured to measure light in a non-gated manner from the time when the laser is projected onto the sample surface until the plasma light is no longer generated, and to measure the non-discrete spectrum only for the wavelength band of 200 nm to 1000 nm. In this case, the spectrometer 21 may remove the reflected light, scattered light, and fluorescence emission, and may effectively obtain the spectrum of the electronic emission from atoms and/or ions and the molecular emission spectrum which are meaningful.

The first optical elements 13 may include media and/or optical elements (for example, a lens) for guiding light and adjusting a focus of light to project the laser onto the sample T.

The second elements 15 may include media and/or optical elements (for example, a lens) for collecting and guiding generated light, and adjusting a focus of light in order to collect generated light and guide the collected light to the cable 31.

The cable 31 may include a light transmission medium for providing a path to allow the generated light collected by the handpiece to travel to the analysis device. The light transmission medium may be configured by an optical fiber, for example.

Figure 6:
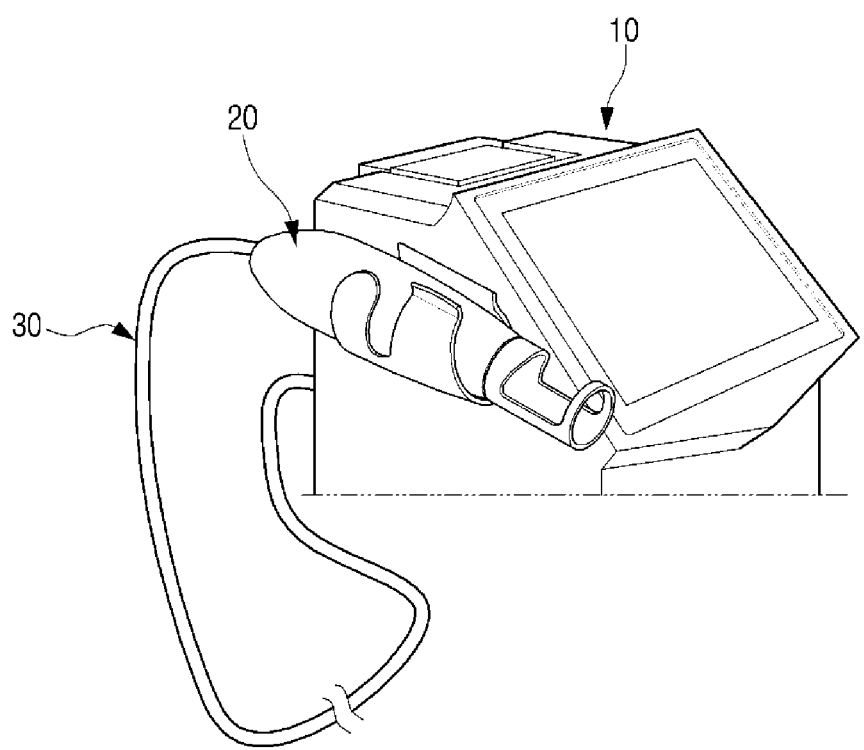
FIG. 6 is a view illustrating an example of the independent device based on the laser spectroscopy for in-vivo detection of lesion tissue described with reference to FIG. 4.

FIG. 6 illustrates an example of the independent device based on the laser spectroscopy for in-vivo lesion tissue detection described above with reference to FIG. 4.

Referring to FIG. 6, the independent device based on the laser spectroscopy for in-vivo lesion tissue detection according to an embodiment of the present disclosure includes an analysis device 10, a handpiece 20, and a cable 30.

The analysis device 10 has a case of a substantially container shape, and may include therein a spectrometer 21, a disease analysis module 23, a power source 25, and a display 27 as described above with reference to FIG. 4.

The handpiece 20 has a shape that is easy to grip with a hand, and may include therein a laser generation device 11, first optical elements 13 for projecting a laser generated by the laser generation device 11 onto body tissue T, and second optical elements 15 for collecting generated light that is generated when the laser is projected onto the body tissue T.

The cable 30 may include an electric wire for providing power and a light transmission medium.

According to an embodiment, the spectrometer 20 may perform non-discrete spectrum measurement with respect to the generated light collected by the second optical elements 15, and the disease analysis module 23 may detect lesion tissue according to the machine learning-based lesion tissue detection method as described above.

According to another embodiment, the spectrometer 20 may measure a filtered non-discrete spectrum for generated light collected by the second optical elements 15, and the disease analysis module 23 may detect lesion tissue according to the machine learning-based lesion tissue detection method as described above.

Regarding the non-discrete spectrum measurement and the machine learning-based lesion tissue detection method, please refer to the above description.

Figure 7:
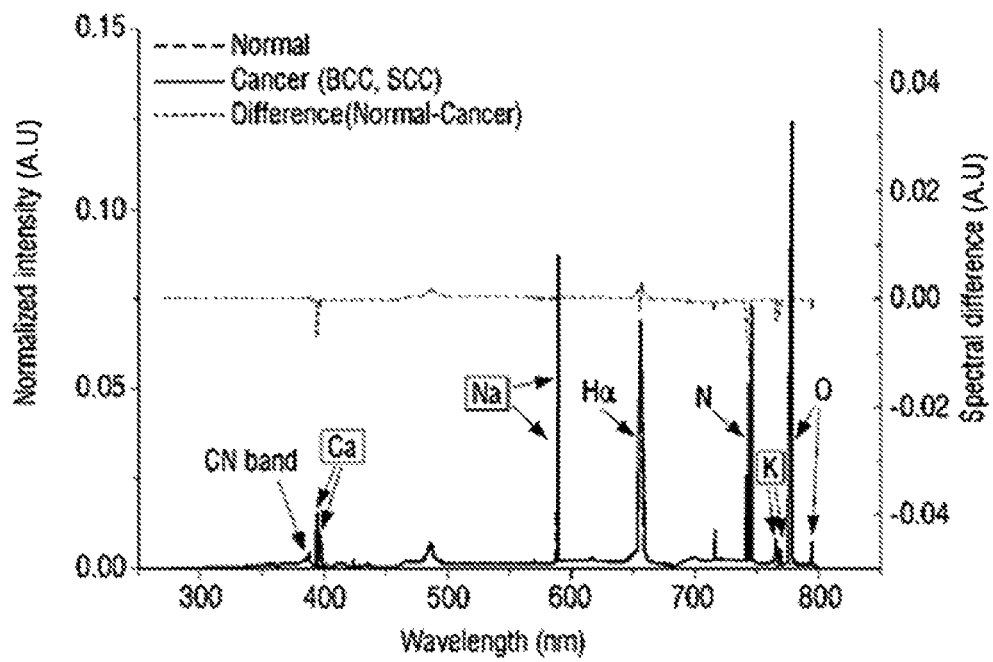
FIGS. 7, 8, and 9 are views to illustrate non-discrete spectrum measurement.
Figure 8:
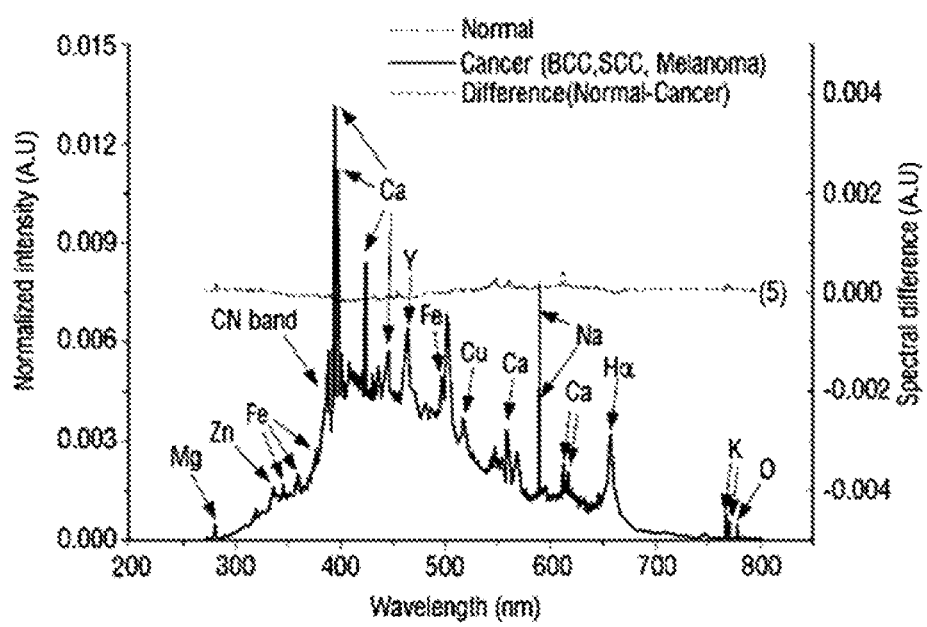
Figure 9:
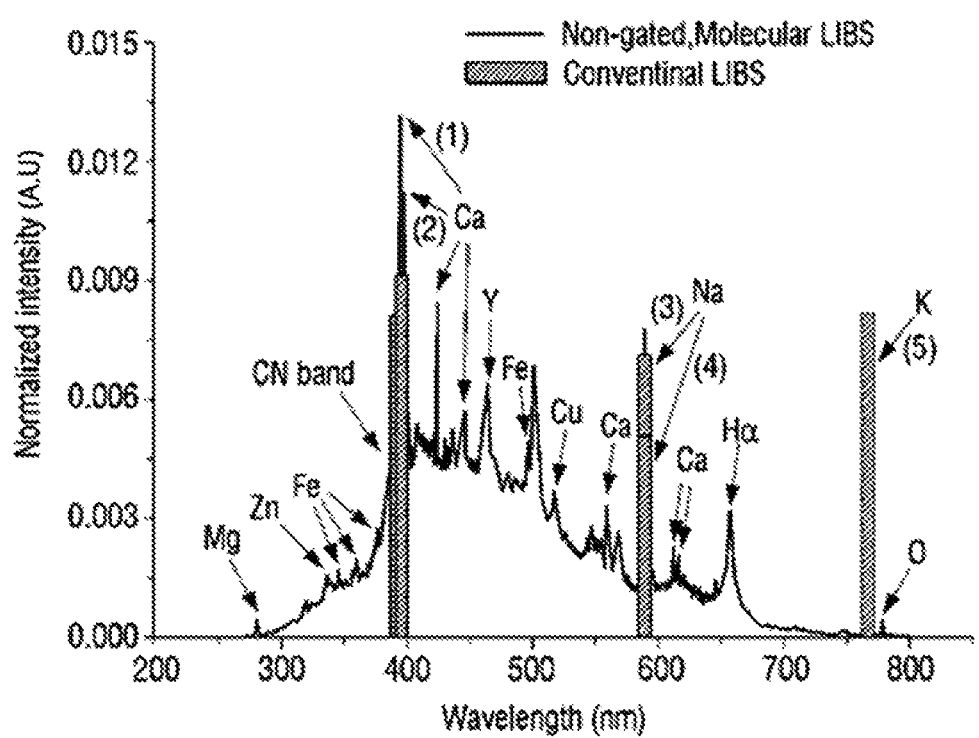

FIGS. 7 to 9 are views to illustrate non-discrete spectrum measurement.

That is, FIG. 7 illustrates a result of related-art discrete spectrum measurement, FIG. 8 illustrates a result of non-discrete spectrum measurement according to an embodiment of the present disclosure, and FIG. 9 illustrates comparison of the results of FIGS. 7 and 8.

Referring to these drawings, the result of the related-art discrete spectrum measurement indicates that only threshold values of wavelength values corresponding to specific components are measured, whereas the result of the non-discrete spectrum measurement according to an embodiment of the present disclosure indicates that values of all wavelength values are measured.

While the invention has been shown and described with reference to certain preferred embodiments thereof and the drawings, the present invention is not limited by the above-described embodiments. It will be understood by those skilled in the art that various changes in form and details may be made therein without departing from the spirit and scope of the invention as defined by the appended claims. Therefore, the scope of the invention is defined not by the detailed description of the invention but by the appended claims and equivalents thereto.

What is claimed is:

1. A Laser-Induced Breakdown Spectroscopy (LIBS) based diagnostic device, the diagnostic device comprising:
    a spectrometer configured to:
        receive plasma light generated due to plasma ablation from after a pulsed laser beam applied on a target tissue by a non-gated manner, wherein the plasma ablation is induced at the target tissue by the pulsed laser beam and the pulsed laser beam is outputted from a laser generation module and is projected onto a skin of a subject,
        obtain spectrum data related to the plasma light received from after the pulsed laser beam applied on the target tissue, wherein the spectrum data includes both of 1) a first spectrum data related to the continuum emission and having overall intensity values within a specific wavelength band, and 2) a second spectrum information related to the element specific emission and having intensity values of spectral peaks within the specific wavelength band, and
    a processor configured to:
        obtain, from the spectrometer, the spectrum data,
        extract a feature data from the spectrum data, wherein the feature data includes a first set of intensity values corresponding to a first plurality of wavelengths related to the related continuum emission and a second set of intensity values corresponding to a second plurality of wavelengths related to the spectral peaks, and the first plurality of wavelengths includes wavelengths disposed between each wavelengths reflecting the spectral peaks within the specific wavelength band
        obtain input data for a deep learning algorithm based on the feature data, wherein the input data includes both the at least part of the first set of intensity values and the at least part of the second set of intensity values, and the each intensity value of each wavelength included in the input data is for inputted each nodes of the deep learning algorithm and the number of intensity values of the input data corresponds to the number of the input nodes of the deep learning algorithm, and
        provide, using the deep learning algorithm, information on whether the target tissue is a lesion tissue related to a skin cancer based on the input data, wherein the deep learning algorithm has been trained with training-data, which is related to plasma ablation induced at a cancerous sample and is labeled with a value indicating cancer, wherein the training data includes both of 1) a third spectrum data related to a continuum emission related to the plasma ablation induced at the cancerous sample and having overall intensity values within the specific wavelength band, and 2) a fourth spectrum data information related to element specific emission to the plasma ablation induced at the cancerous sample and having intensity values of spectral peaks within the specific wavelength band.

2. The diagnostic device of claim 1, wherein the specific wavelength band is set to be between 200 nm and 1000 nm.

3. The diagnostic device of claim 1, wherein a wavelength of the pulsed laser beam applied by the laser generation module is set to be a specific wavelength out of the specific wavelength band.

4. The diagnostic device of claim 1, wherein the skin cancer includes at least one of squamous cell carcinoma, basal cell carcinoma, or melanoma.

5. A Laser-Induced Breakdown Spectroscopy (LIBS) based diagnostic device, the diagnostic device comprising:
    a laser generation module configured to apply a pulsed laser beam onto a target object to induce plasma ablation at the target object, wherein the target object is a part of a body of a subject;
    a spectrometer configured to:
        receive light generated due to the plasma ablation from after the pulsed laser beam applied on the target object by non-gated manner, and
        obtain target spectrum data related to the light received from after the pulsed laser beam applied on the target object, wherein the target spectrum data includes both of 1) a first spectrum data related to the continuum emission and having overall intensity values within a specific wavelength band, and 2) a second spectrum data related to the element specific emission and having intensity values of spectral peaks within the specific wavelength band, and
    a processor configured to:
    obtain, from the spectrometer, the target spectrum data,
    extract a feature data from the target spectrum data, wherein the feature data includes a first set of intensity values corresponding to a first plurality of wavelengths related to the related continuum emission and a second set of intensity values corresponding to a second plurality of wavelengths related to the spectral peaks, and the first plurality of wavelengths are except the spectral peaks within the specific wavelength band,
    obtain input data for a deep learning algorithm based on the feature data, wherein the input data includes both the at least of the first set of intensity values and the at least part of the second set of intensity values, and the each intensity value of each wavelength included in the input data is for inputted input nodes of the deep learning algorithm and the number of intensity values of the input data corresponds to the number of the input nodes of the deep learning algorithm, and
    provide, using the deep learning algorithm, diagnostic information on whether the target object is a lesion tissue related to a skin cancer based on the target input data, wherein the deep learning algorithm has been trained with training-data, which is related to plasma ablation induced at a cancerous sample and is labeled with a value indicating cancer, wherein the training data includes both of 1) a third spectrum data related to a continuum emission related to the plasma ablation induced at the cancerous sample and having overall intensity values within the specific wavelength band for the predetermined wavelength range and 2) a fourth spectrum data related to element specific emission related to the plasma ablation induced at the cancerous sample and having intensity values of spectral peaks within the specific wavelength band.

6. The diagnostic device of claim 5, wherein the specific wavelength band is set to be between 200 nm and 1000 nm.

7. The diagnostic device of claim 5, wherein a wavelength of the pulsed laser beam applied by the laser generation module is set to be a specific wavelength out of the specific wavelength band.

8. The diagnostic device of claim 5, and wherein the skin cancer includes at least one of squamous cell carcinoma, basal cell carcinoma, or melanoma.

* * * * *